(12) United States Patent
Brocke et al.

(10) Patent No.: US 11,208,595 B2
(45) Date of Patent: Dec. 28, 2021

(54) LIQUID-CRYSTALLINE COMPOUNDS

(71) Applicant: Merck Patent GmbH, Darmstadt (DE)

(72) Inventors: Constanze Brocke, Gross-Gerau (DE); Katharina Linke, Rodgau (DE); Sven Christian Laut, Weiterstadt (DE)

(73) Assignee: Merck Patent GmbH, Darmstadt (DE)

(*) Notice: Subject to any disclaimer, the term of this patent is extended or adjusted under 35 U.S.C. 154(b) by 15 days.

(21) Appl. No.: 16/820,916

(22) Filed: Mar. 17, 2020

(65) Prior Publication Data
US 2020/0299580 A1    Sep. 24, 2020

(30) Foreign Application Priority Data

Mar. 18, 2019   (DE) .......................... 102019001887.7

(51) Int. Cl.
| | | |
|---|---|---|
| G02F 1/1333 | (2006.01) | |
| C09K 19/34 | (2006.01) | |
| C07D 309/04 | (2006.01) | |
| C07D 319/06 | (2006.01) | |

(52) U.S. Cl.
CPC ........ C09K 19/3402 (2013.01); C07D 309/04 (2013.01); C07D 319/06 (2013.01); *C09K 2019/3422* (2013.01)

(58) Field of Classification Search
CPC .... C09K 19/34; C09K 19/44; C09K 19/3402; C09K 19/0233; C09K 19/3098; C09K 2019/3422; G02F 1/13; G02F 1/1333; C07D 309/04; C07D 319/06
See application file for complete search history.

(56) References Cited

U.S. PATENT DOCUMENTS

| | | |
|---|---|---|
| 7,361,388 B2 | 4/2008 | Kirsch et al. |
| 2006/0289829 A1 | 12/2006 | Kirsch et al. |
| 2018/0022999 A1* | 1/2018 | Ookawa ............... C07C 43/184 349/33 |
| 2020/0299580 A1* | 9/2020 | Brocke .............. C09K 19/3402 |

FOREIGN PATENT DOCUMENTS

| | | |
|---|---|---|
| WO | 2004/106460 A1 | 12/2004 |
| WO | 2018/141759 A1 | 8/2018 |

* cited by examiner

*Primary Examiner* — Geraldina Visconti
(74) *Attorney, Agent, or Firm* — Millen White Zelano and Branigan, PC; John Sopp

(57) ABSTRACT

Compounds of the formula I,

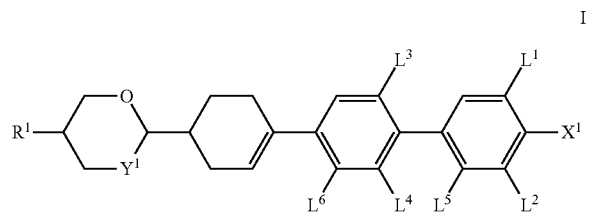

in which $Y^1$ denotes —O— or —$CH_2$—, and the groups $R^1$, $L^1$ to $L^6$ and $X^1$ have the meanings indicated in claim 1. A process for the preparation thereof, and liquid-crystalline media comprising at least one compound of the formula I and electro-optical displays containing a liquid-crystalline medium this type. The compounds of the formula I include, as structural element, a combination of a 1,4-substituted cyclohexene ring besides a dioxane or tetrahydropyran ring and a substituted biphenyl group.

15 Claims, No Drawings

LIQUID-CRYSTALLINE COMPOUNDS

An aspect of the invention relates to compounds of the formula I as defined below, which contain, as structural elements, a combination of a 1,4-substituted cyclohexene ring besides a dioxane or tetrahydropyran ring and a substituted biphenyl group. In addition, the invention encompasses a process for the preparation of these compounds, liquid-crystalline media comprising at least one compound of the formula I, and the use thereof as component(s) in liquid-crystalline media. In addition, the present invention relates to liquid-crystal and electro-optical display elements which contain the liquid-crystalline media according to the invention.

In previous years, the areas of application for liquid-crystalline compounds have been considerably expanded to various types of display devices, electro-optical devices, electronic components, sensors, etc. For this reason, a number of different structures have been proposed, in particular in the area of nematic liquid crystals. The nematic liquid-crystal mixtures have to date found the broadest use in flat-panel display devices. They have been employed, in particular, in passive TN or STN matrix displays or systems having a TFT active matrix.

The liquid-crystalline compounds according to the invention can be used as component(s) of liquid-crystalline media, in particular for displays based on the principle of the twisted cell, the guest-host effect, the effect of deformation of aligned phases DAP or ECB (electrically controlled birefrin-gence), the IPS (in-plane switching) effect or the effect of dynamic scattering.

The use of polar dioxane and tetrahydropyran compounds having four rings as liquid-crystalline substances is not unknown to the person skilled in the art. Various compounds containing an O-heterocyclic ring have already been described as liquid-crystalline or mesogenic material, as has the preparation thereof, such as, for example, in the publication WO 2004/106460 A1. The compounds proposed therein do not contain a cyclohexene ring. As polar end group, the compounds contain, for example, —OCF$_3$ or fluorine.

Cyclohexene compounds containing a dioxane ring are known from WO 2018/141759 A1, but contain in total only three ring groups.

An object of the present invention was finding novel stable compounds which are suitable as component(s) of liquid-crystalline media. In particular, the compounds should simultaneously have a comparatively low viscosity as well as high dielectric anisotropy. For many current mixture concepts in the area of liquid crystals, it is advantageous to use compounds having positive dielectric anisotropy $\Delta\varepsilon$ in combination with moderate to high optical anisotropy.

In view of the very wide variety of areas of application of compounds of this type having high $\Delta\varepsilon$, it was desirable to have available further compounds, preferably having a high clearing point and low viscosity, which have properties which are precisely tailored to the respective applications.

It was thus an object of the invention to find novel stable compounds which are suitable as component(s) of liquid-crystalline media, in particular for, for example, TN, STN, IPS, FFS and TN-TFT displays.

In addition, it was an aim for the compounds according to the invention to be thermally and photochemically stable under the conditions prevailing in the areas of application. As mesogens, they should facilitate a broad nematic phase in mixtures with liquid-crystalline co-components and be readily miscible with nematic base mixtures, in particular at low temperatures. Preference is likewise given to substances having a low melting point and a low enthalpy of melting, since these parameters are in turn signs of the desirable properties mentioned above, such as, for example, high solubility, a broad liquid-crystalline phase and a low tendency towards spontaneous crystallisation in mixtures at low temperatures. In particular, the solubility at low temperature, while avoiding any crystallisation, is important for safe operation and transport of displays in vehicles, aircraft and outdoors.

Surprisingly, it has been found that the compounds according to the invention are eminently suitable as components of liquid-crystalline media. They can be used to obtain liquid-crystalline media for displays which require particularly high dielectric anisotropies, in particular for IPS or FFS displays, but also for TN or STN displays. The compounds according to the invention are sufficiently stable and colourless. In particular, they are distinguished by high dielectric anisotropies ($\Delta\varepsilon$), owing to which smaller layer thicknesses and thus lower threshold voltages are necessary on use in optical switching elements. They have good solubility for compounds having comparable properties. In addition, the compounds according to the invention have a comparatively very high clearing point and at the same time low values for the rotational viscosity. The compounds have relatively low melting points. By means of the compounds according to the invention, it is surprisingly possible to prepare liquid-crystalline mixtures having high values of the elastic constants ($K^{11}/K^{22}/K^{33}$) and a low ratio of the rotational viscosity to the elastic constant $K^{11}$ without adversely affecting the other use parameters. This gives media having a short response time and high contrast.

The provision of the compounds according to the invention very generally considerably broadens the range of liquid-crystalline substances that are suitable, from various applicational points of view, for the preparation of liquid-crystalline mixtures.

The compounds according to the invention have a broad range of applications. Depending on the choice of substituents, these compounds can serve as base materials of which liquid-crystalline media are predominantly composed. However, it is also possible to add liquid-crystalline base materials from other classes of compound to the compounds of the formula I according to the invention in order, for example, to influence the dielectric and/or optical anisotropy of a dielectric of this type and/or to optimise its threshold voltage and/or its viscosity.

The invention thus relates to compounds of the formula I,

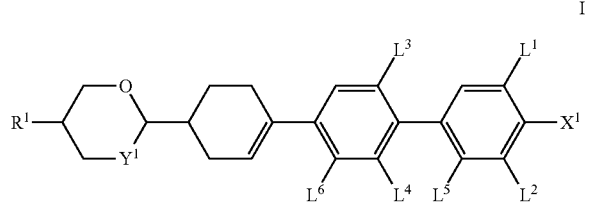

in which
X$^1$ denotes F, CF$_3$, OCF$_3$, Cl, OCHF$_2$, CHF$_2$, SCN or CN,
Y$^1$ denotes O or CH$_2$,
R$^1$ denotes an alkyl radical having 1 to 15 C atoms, where, in addition, one or more CH$_2$ groups in these radicals may in each case be replaced, independently of one another, by —C≡C—, —CF$_2$O—, —OCF$_2$—, —CH=CH—,

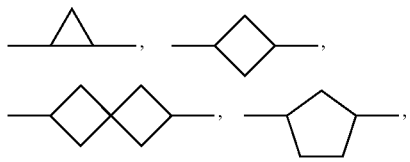

—O—, —S—, —CO—O— or —O—CO— in such a way that O/S atoms are not linked directly to one another, and in which, in addition, one or more H atoms may be replaced by halogen, or denotes H, preferably R$^1$ is a halogenated or unsubstituted alkyl radical having 1 to 15 C atoms, where, in addition, one or more CH$_2$ groups in these radicals may in each case be replaced, independently of one another, by —C≡C— or —CH=CH—, and L$^1$ and L$^2$, independently of one another, denote H or F, preferably F, L$^3$ denotes H or F, preferably F, L$^4$ denotes H or F, preferably H, and L$^5$ and L$^6$, independently of one another, denote H or CH$_3$, preferably H.

The invention furthermore relates to the use of the compounds of the formula I in liquid-crystalline media.

The present invention likewise relates to liquid-crystalline media having at least two liquid-crystalline components which comprise at least one compound of the formula I.

In the pure state, the compounds of the formula I are colourless and, per se or in mixtures, form liquid-crystalline mesophases in a temperature range which is favourably located for electro-optical use. The compounds according to the invention enable broad nematic phase ranges to be achieved. In liquid-crystalline mixtures, the substances according to the invention significantly increase the optical anisotropy and/or result in an improvement in the low-temperature storage stability compared with comparable mixtures having high dielectric anisotropy. At the same time, the compounds are distinguished by good UV stability.

The radical R$^1$ in the formula I and sub-formulae thereof preferably denotes alkyl having 1 to 8 carbon atoms or alkenyl having 2 to 8 carbon atoms. R$^1$ particularly preferably denotes a straight-chain alkyl radical having 1 to 7 C atoms or an unbranched alkenyl radical having 2 to 8 C atoms, in particular unbranched alkyl having 1 to 5 C atoms.

Alternative preferred radicals R$^1$ are selected from cyclopentyl, 2-fluoroethyl, cyclopropylmethyl, cyclopentylmethyl, cyclopentylmethoxy, cyclobutylmethyl, 2-methylcyclopropyl, 2-methylcyclobutyl and 2-alkyloxyethoxy.

The radical X$^1$ of the formula I preferably denotes F, CF$_3$, OCF$_3$ or —SCN, particularly preferably F, CF$_3$ or OCF$_3$, and very particularly preferably F.

Compounds of the formula I containing branched or substituted wing groups R$^1$ may occasionally be of importance owing to better solubility in the conventional liquid-crystalline base materials. The group R$^1$ is preferably straight-chain.

Preference is given to compounds of the formula I in which L$^1$ denotes F and L$^2$ denotes H or F, in particular in which L$^1$ and L$^2$ denote F. Preference is furthermore given to compounds in which L$^3$ denotes H or F and L$^4$ denotes H, in particular L$^3$=H and L$^4$=F. Preference is furthermore given to compounds in which L$^6$ denotes H and L$^5$ denotes H or methyl, in particular L$^5$ and L$^6$=H.

The radical R$^1$ is particularly preferably selected from the moieties:

—CH$_3$

—C$_2$H$_5$

—C$_3$H$_7$

—C$_4$H$_9$

—C$_5$H$_{11}$

—C$_6$H$_{13}$

—CH=CH$_2$

—CH=CH$_2$—CH$_3$

—CH$_2$—CH$_2$—CH=CH$_2$

—CH$_2$—CH$_2$—CH=CH—CH$_3$ in which the alkyl chains are preferably unbranched (n-alkyl).

Particularly preferred compounds of the formula I are the compounds of the formulae I-1 to I-6:

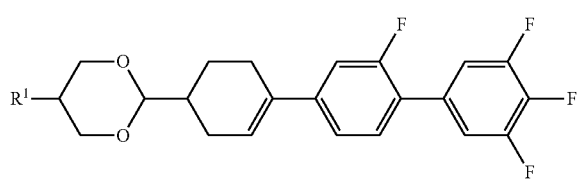

I-1

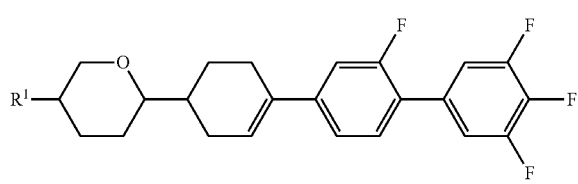

I-2

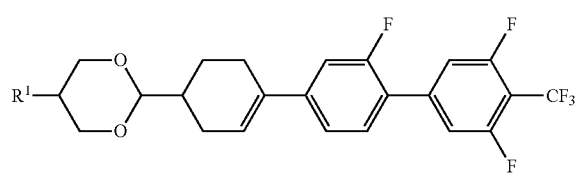

I-3

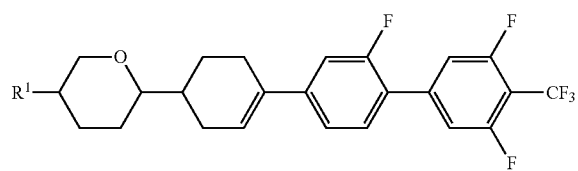

I-4

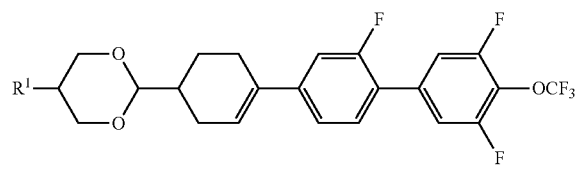

I-5

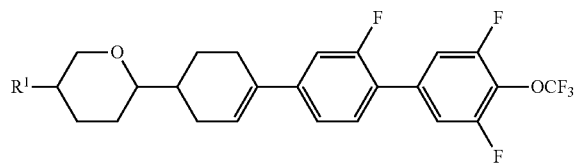
in which R¹ independently has the meanings indicated above. Of the compounds of the formulae I-1 to I-6, preference is given to the compounds of the formulae I-1 and I-2. R¹ particularly preferably denotes an n-alkyl group having 2, 3, 4, 5, 6 or 7 C atoms.
Illustrative compounds are of the following formulae:
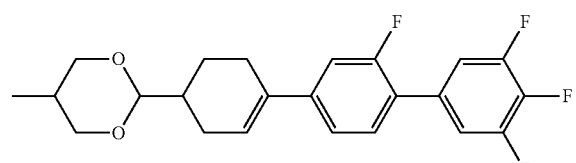
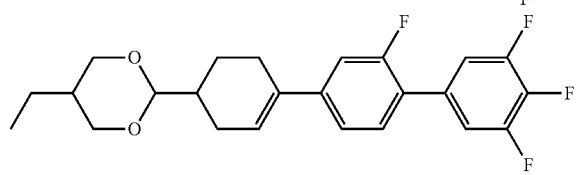
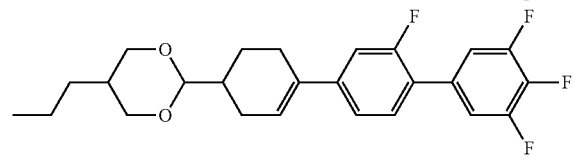
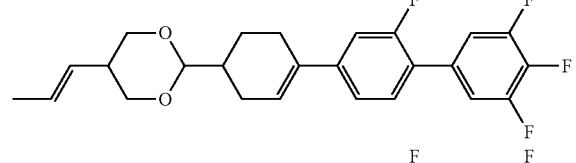
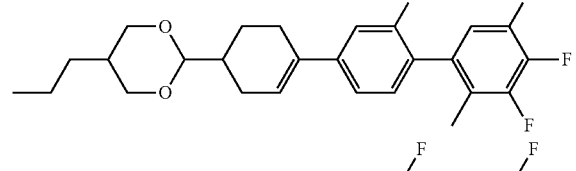
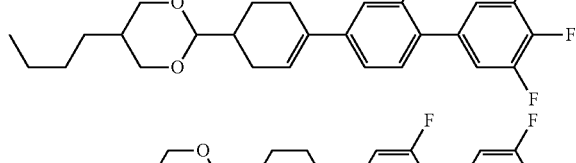
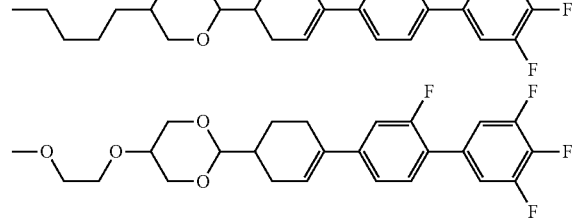
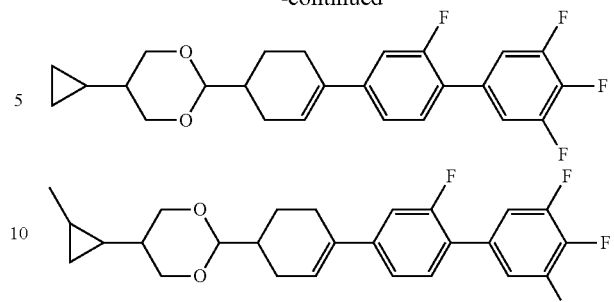

-continued

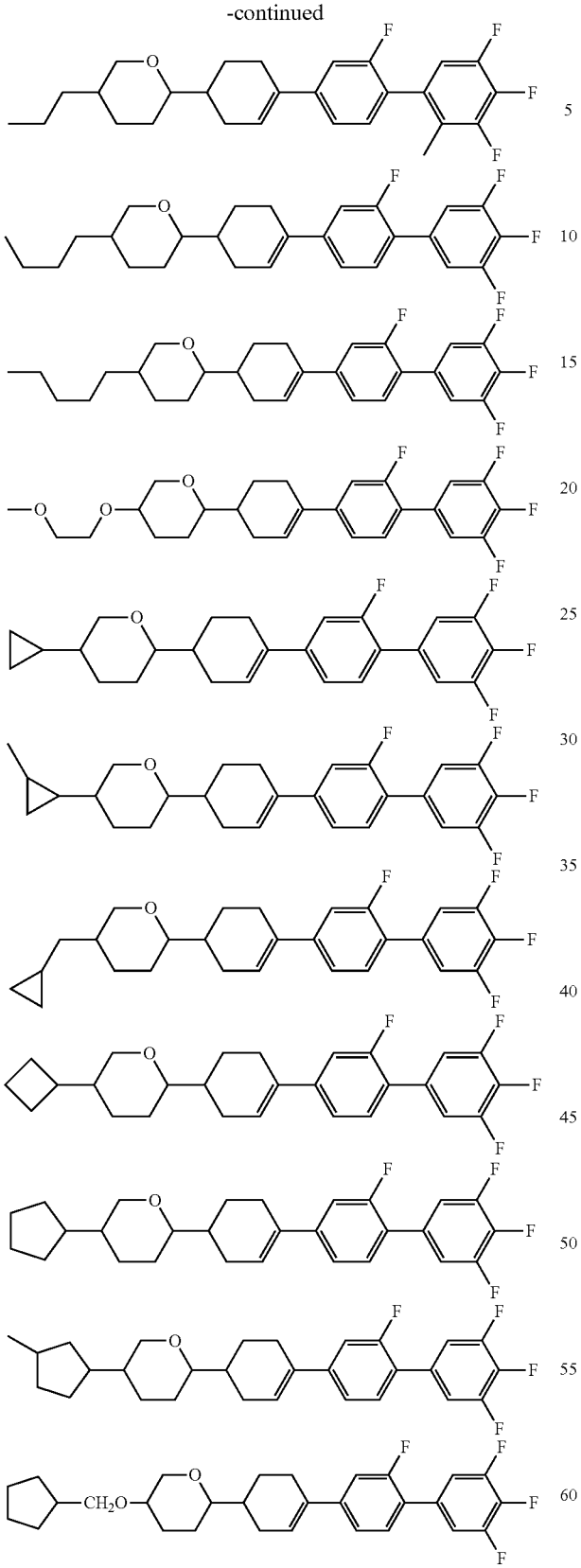

The compounds of the formula I can be prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se, which are not mentioned here in greater detail.

Compounds of the formula I can advantageously be prepared as shown in the following illustrative synthesis and the examples (schemes 1 to 3):

Scheme 1. General synthesis scheme for the preparation of dioxane compounds of the formula I ($Y^1$ = O). $R_1$ and $X_1$ are defined in accordance with formula I.

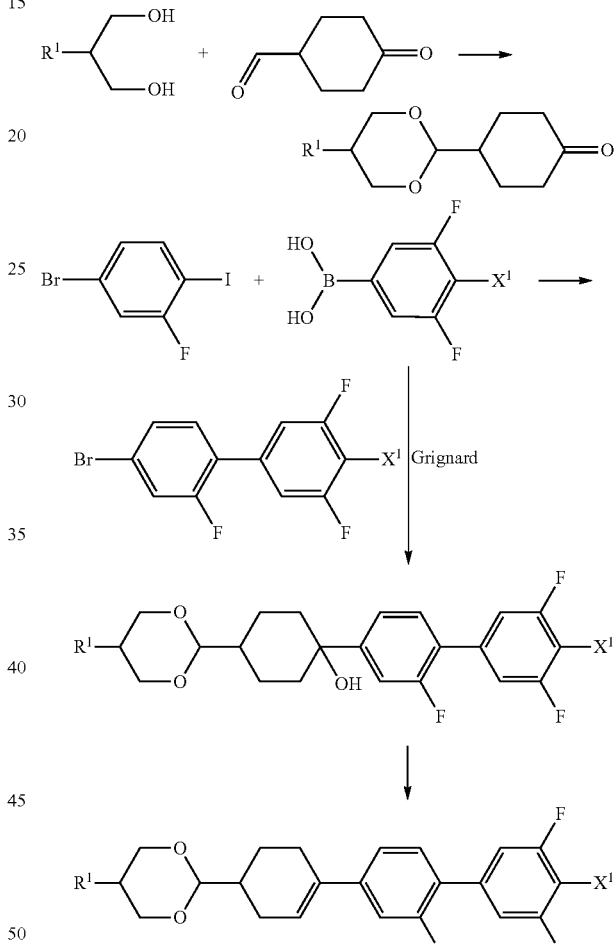

Modification of the reaction sequence from scheme 1 alternatively gives synthesis scheme 2 for the preparation of corresponding tetrahydropyran compounds.

Scheme 2. General synthesis scheme for the preparation of compounds of the formula I in which $Y^1$ = $CH_2$ (2,5-tetrahydropyran derivatives). $R^1$ and $X^1$ are defined in accordance with formula I.

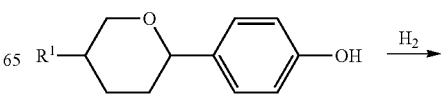

-continued

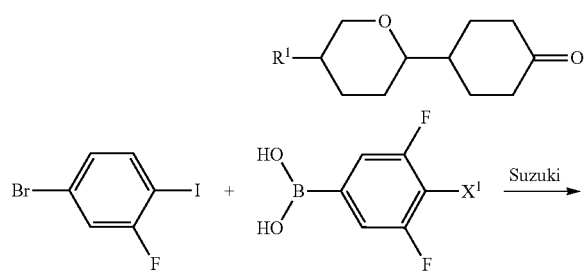

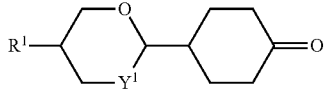

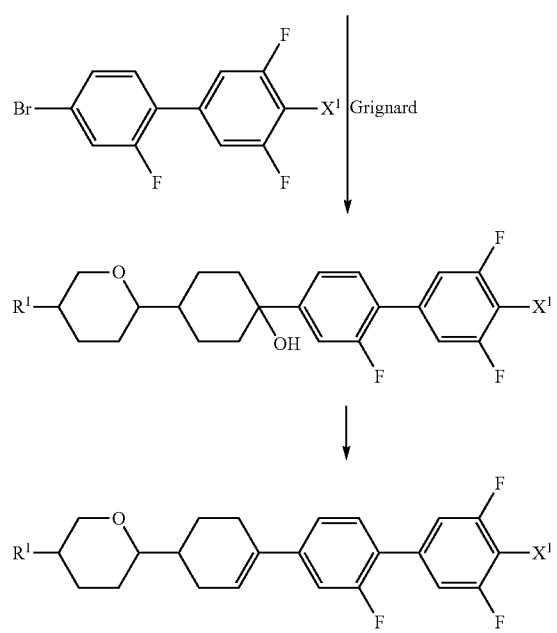

Corresponding starting materials can generally readily be prepared by the person skilled in the art by synthetic methods known from the literature or are commercially available.

Instead of the outlined Grignard compounds according to Schemes 1 and 2, it is also possible to use aryllithium compounds, which are accessible analogously by halogen-metal exchange with alkyllithium compounds at low temperatures (cf., for example, U.S. Pat. No. 4,940,822).

The invention therefore also relates to a process for the preparation of compounds of the formula I which includes a process step in which an aryl-halogen compound of the formula II

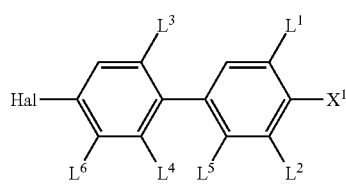

in which $X^1$, $L^1$, $L^2$, $L^3$ and $L^4$ are defined as for formula I, and

Hal denotes Br, I or Cl, preferably Br, is reacted with a compound of the formula III

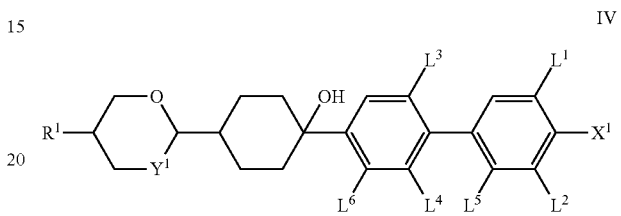

in which $R^1$ and $Y^1$ are defined as for formula I, to give a compound of the formula IV,

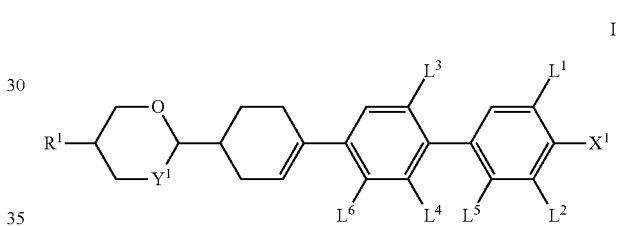

and is further converted into a compound of the formula I

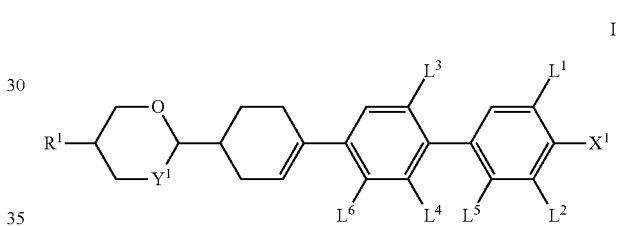

in which the groups are as defined above.

For the reaction of compound II with III, the compound II is generally firstly metallated, for example by reaction with alkylmagnesium halides, magnesium or alkyllithium compounds. The alkylmetal compound is subsequently reacted with the cyclohexyl ketone III. The cyclohexanol product of the formula IV is converted into the cyclohexene of the formula I by elimination of water with acid catalysis.

The reaction methods and reagents used are in principle known from the literature. Further reaction conditions are exemplified by the working examples.

Further preferred process variants, not mentioned above, are revealed by the examples or the claims.

The process and the subsequent work-up of the reaction mixtures obtained by the above processes can basically be carried out as a batch reaction or in a continuous reaction procedure. The continuous reaction procedure encompasses, for example, reaction in a continuous stirred-tank reactor, a stirred-tank reactor cascade, a loop or cross-flow reactor, a flow tube or in a microreactor. The reaction mixtures are optionally worked up, as necessary, by filtration through solid phases, chromatography, separation between immiscible phases (for example extraction), adsorption onto solid supports, removal of solvents and/or azeotropic mixtures by distillation, selective distillation, sublimation, crystallisation, co-crystallisation or by nanofiltration on membranes.

In the present disclosure, the 2,5-disubstituted dioxane ring of the formula

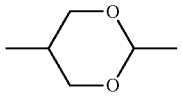

preferably denotes a 2,5-trans-configured dioxane ring, i.e., the substituents R are preferably both in the equatorial position in the preferred chair conformation. The 2,5-disubstituted tetrahydropyran of the formula

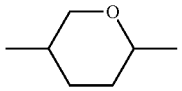

likewise preferably denotes a 2,5-trans-configured tetrahydropyran ring, i.e., the substituents are preferably both in the equatorial position in the preferred chair conformation.

The invention also relates to liquid-crystalline media comprising one or more of the compounds of the formula I according to the invention. The liquid-crystalline media comprise at least two components. They are preferably obtained by mixing the components with one another. A process according to the invention for the preparation of a liquid-crystalline medium is therefore characterised in that at least one compound of the formula I is mixed with at least one further mesogenic compound, and additives are optionally added.

The achievable combinations of clearing point, viscosity at low temperature, thermal/UV stability, dielectric anisotropy, response time and contrast for liquid-crystalline media containing the compounds of formula I are far superior to previous materials from the prior art.

The liquid-crystalline media according to the invention preferably comprise 2 to 40, particularly preferably 4 to 30, components as further constituents besides one or more compounds according to the invention. In particular, these media comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexanes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most preferred compounds suitable as further constituents of the media according to the invention can be characterised by the formulae 1, 2, 3, 4 and 5:

R'-L-E-R''                1

R'-L-COO-E-R''            2

R'-L-CF$_2$O-E-R''         3

R'-L-CH$_2$CH$_2$-E-R''    4

In the formulae 1, 2, 3, 4 and 5, L and E, which may be identical or different, each, independently of one another, denote a divalent radical from the group formed by the structural elements -Phe-, -Cyc-, -Phe-Phe-, -Phe-Cyc-, -Cyc-Cyc-, -Pyr-, -Dio-, -Py-, -G-Phe-, -G-Cyc- and their mirror images, where Phe denotes unsubstituted or fluorine-substituted 1,4-phenylene, Cyc denotes trans-1,4-cyclohexylene, Pyr denotes pyrimidine-2,5-diyl or pyridine-2,5-diyl, Dio denotes 1,3-dioxane-2,5-diyl, Py denotes tetrahydropyran-2,5-diyl and G denotes 2-(trans-1,4-cyclohexyl)ethyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe, Py and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

R' and/or R'' each, independently of one another, denote alkyl, alkenyl, alkoxy, alkoxyalkyl, alkenyloxy or alkanoyloxy having up to 8 C atoms, —F, —Cl, —CN, —NCS or —(O)$_i$CH$_{3-k}$F$_k$, where i is 0 or 1 and k is 1, 2 or 3.

In a smaller sub-group of the compounds of the formulae 1, 2, 3, 4 and 5, R' and R'' each, independently of one another, denote alkyl, alkenyl, alkoxy, alkoxyalkyl, alkenyloxy or alkanoyloxy having up to 8 C atoms. This smaller sub-group is called group A below, and the compounds are referred to by the sub-formulae 1a, 2a, 3a, 4a and 5a. In most of these compounds, R' and R'' are different from one another, one of these radicals usually being alkyl, alkenyl, alkoxy or alkoxyalkyl.

In another smaller sub-group of the compounds of the formulae 1, 2, 3, 4 and 5, which is referred to as group B, R'' denotes —F, —Cl, —NCS or —(O)$_i$CH$_{3-k}$F$_k$, where i is 0 or 1 and k is 1, 2 or 3. The compounds in which R'' has this meaning are referred to by the sub-formulae 1 b, 2b, 3b, 4b and 5b. Particular preference is given to those compounds of the sub-formulae 1 b, 2b, 3b, 4b and 5b in which R'' has the meaning —F, —Cl, —NCS, —CF$_3$, —OCHF$_2$ or —OCF$_3$.

In the compounds of the sub-formulae 1 b, 2b, 3b, 4b and 5b, R' has the meanings indicated in the case of the compounds of the sub-formulae 1a to 5a and is preferably alkyl, alkenyl, alkoxy or alkoxyalkyl.

In a further smaller sub-group of the compounds of the formulae 1, 2, 3, 4 and 5, R'' denotes —CN. This sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' has the meanings indicated in the case of the compounds of the sub-formulae 1a to 5a and is preferably alkyl, alkoxy or alkenyl.

Besides the preferred compounds of groups A, B and C, other compounds of the formulae 1, 2, 3, 4 and 5 having other variants of the proposed substituents are also customary. All these substances are obtainable by methods which are known from the literature or analogously thereto.

Besides compounds of the formula I according to the invention, the media according to the invention preferably comprise one or more compounds selected from groups A, B and/or C. The proportions by weight of the compounds from these groups in the media according to the invention are preferably:

group A: 0 to 90%, preferably 20 to 90%, particularly preferably 30 to 90%;
group B: 0 to 80%, preferably 10 to 80%, particularly preferably 10 to 65%;
group C: 0 to 80%, preferably 0 to 80%, particularly preferably 0 to 50%;

where the sum of the proportions by weight of the group A, B and/or C compounds present in the respective media according to the invention is preferably 5 to 90% and particularly preferably 10 to 90%.

The media according to the invention preferably comprise 1 to 40%, particularly preferably 3 to 30%, of the compounds according to the invention.

The liquid-crystal mixtures according to the invention are prepared in a manner which is conventional per se. In general, the desired amount of the components used in lesser amount is dissolved in the components making up the principal constituent, preferably at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multibottle" systems.

The liquid-crystal mixtures may also comprise further additives known to the person skilled in the art and described in the literature. For example, 0 to 15%, preferably 0 to 10%, of pleochroic dyes, chiral dopants, stabilisers or nanoparticles can be added. The individual compounds added are employed in concentrations of 0.01 to 6%, preferably 0.1 to 3%. However, the concentration data of the other constituents of the liquid-crystal mixtures, i.e. the liquid-crystalline or mesogenic compounds, are given here without taking into account the concentration of these additives.

The liquid-crystal mixtures according to the invention enable a significant broadening of the available parameter latitude.

The invention also relates to electro-optical displays (in particular TFT displays having two plane-parallel outer plates, which, together with a frame, form a cell, integrated non-linear elements for switching individual pixels on the outer plates, and a nematic liquid-crystal mixture having positive dielectric anisotropy and high specific resistance located in the cell) which contain media of this type, and to the use of these media for electro-optical purposes.

The expression "alkyl" encompasses unbranched and branched alkyl groups having 1-15 carbon atoms, in particular the unbranched groups methyl, ethyl, n-propyl, n-butyl, n-pentyl, n-hexyl and n-heptyl. Groups having 2-5 carbon atoms are generally preferred.

The expression "alkenyl" encompasses unbranched and branched alkenyl groups having up to 15 carbon atoms, in particular the unbranched groups. Particularly preferred alkenyl groups are $C_2$-$C_7$-1E-alkenyl, $C_4$-$C_7$-$C_3$E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having 2 to 5 carbon atoms are generally preferred.

The expression "halogenated alkyl radical" preferably encompasses mono- or polyfluorinated and/or -chlorinated radicals. Perhalogenated radicals are included. Particular preference is given to fluorinated alkyl radicals, in particular $CF_3$, $CH_2CF_3$, $CH_2CHF_2$, $CHF_2$, $CH_2F$, $CHFCF_3$ and $CF_2CHFCF_3$. The expression "halogenated alkenyl radical" and related expressions are explained correspondingly.

The total amount of compounds of the formula I in the mixtures according to the invention is not crucial. The mixtures may therefore comprise one or more further components for the purposes of optimisation of various properties.

The construction of a matrix display according to the invention from polarisers, electrode base plates and surface-treated electrodes corresponds to the usual design for displays of this type. The term usual design is broadly drawn here and also encompasses all derivatives and modifications of the matrix display, in particular also matrix display elements based on poly-Si TFTs.

An essential difference between the displays according to the invention and the hitherto conventional ones based on the twisted nematic cell consists, however, in the choice of the liquid-crystal parameters of the liquid-crystal layer.

The following examples explain the invention without intending to restrict it. The person skilled in the art will be able to glean from the examples working details that are not given in detail in the general description, generalise them in accordance with general expert knowledge and apply them to a specific problem.

Above and below, percentage data denote percent by weight. All temperatures are indicated in degrees Celsius. Furthermore, C=crystalline state, N=nematic phase, Sm=smectic phase (more especially SmA, SmB, etc.), Tg=glass-transition temperature and I=isotropic phase. The data between these symbols represent the transition temperatures. $\Delta n$ denotes optical anisotropy (589 nm, 20° C.), $\Delta \varepsilon$ the dielectric anisotropy (1 kHz, 20° C.) and $\gamma_1$ the rotational viscosity (20° C.; in the unit mPa·s).

The physical, physicochemical and electro-optical parameters are determined by generally known methods, as described, inter alia, in the brochure "Merck Liquid Crystals—Licristal®—Physical Properties of Liquid Crystals—Description of the Measurement Methods", 1998, Merck KGaA, Darmstadt.

The dielectric anisotropy $\Delta \varepsilon$ of the individual substances is determined at 20° C. and 1 kHz. To this end, 5-10% by weight of the substance to be investigated are measured dissolved in the dielectrically positive mixture ZLI-4792 (Merck KGaA), and the measurement value is extrapolated to a concentration of 100%. The optical anisotropy $\Delta n$ is determined at 20° C. and a wavelength of 589.3 nm, the rotational viscosity $\gamma_1$ at 20° C., both likewise by linear extrapolation.

In the present application, unless expressly indicated otherwise, the plural form of a term denotes both the singular form and the plural form, and vice versa. Further combinations of the embodiments and variants of the invention in accordance with the description also arise from the appended claims or from combinations of a plurality of these claims.

The following abbreviations are used:
RT room temperature
THF tetrahydrofuran
MTB-Ether methyl tert-butyl ether
sat. saturated
dist. distilled

EXAMPLES

The present invention is described in detail by the following non-restrictive examples.

Example 1

2-[4-[3-Fluoro-4-(3,4,5-trifluorophenyl)phenyl]cyclohex-3-en-1-yl]-5-propyl-1,3-dioxane

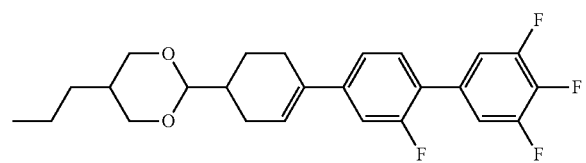 [SMILES: CCCC1COC(C2CC=C(c3ccc(-c4cc(F)c(F)c(F)c4)c(F)c3)CC2)OC1]

Step 1.1: 4-(5-Propyl-1,3-dioxan-2-yl)cyclohexanone

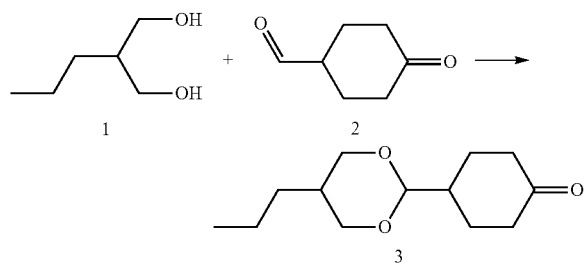

Toluene-4-sulfonic acid monohydrate (6.4 g, 32 mmol) is added to a solution of 2-propylpropane-1,3-diol 1 (23.9 g, 193 mmol) and 4-oxocyclo-hexanecarbaldehyde 2 (CAS 96184-81-5, 30.0 g, 170 mmol) in dichloromethane (270 ml), and the mixture is reflux on a water separator. After 90 min, the reaction mixture is cooled to RT and chromatographed over silica gel (dichloromethane/ethyl acetate 9:1). 4-(5-Propyl-1,3-dioxan-2-yl)-cyclohexanone 3 is isolated as a yellow, clear oil which solidifies to give a crystal mass.

Step 1.2: 1-[3-Fluoro-4-(3,4,5-trifluorophenyl)phenyl]-4-(5-propyl-1,3-dioxan-2-yl)cyclohexanol

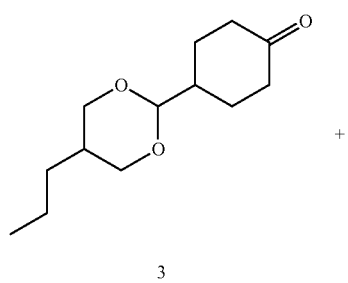

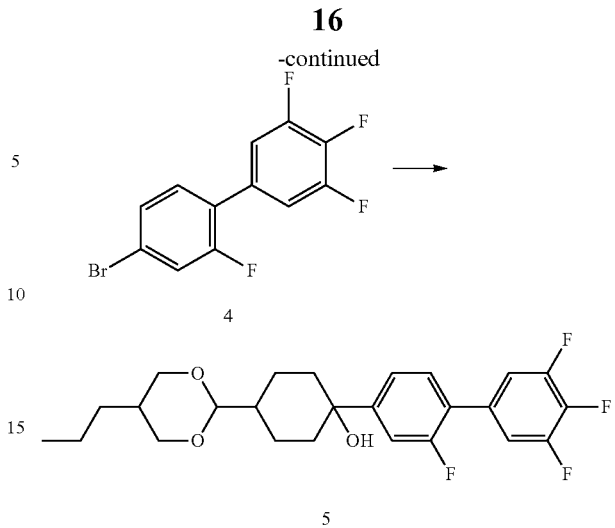

A solution of isopropylmagnesium chloride/lithium chloride (116 ml, 150 mmol, 1.3 mol/l in THF) is initially introduced, and a solution of 5-(4-bromo-2-fluorophenyl)-1,2,3-trifluorobenzene 4 (CAS 187804-77-9, 25.0 g, 80 mmol) in THF (150 ml) is added dropwise at 30° C. After 60 min, a solution of 4-(5-propyl-1,3-dioxan-2-yl)cyclohexanone 3 (25.0 g, 80 mmol) in THF (150 ml) is added dropwise at a maximum of 30° C. After a further 60 min, dist. water is added to the reaction mixture, which is then adjusted to pH=5 using hydrochloric acid (1 M). The aqueous phase is separated off and extracted with MTB ether. The combined organic phases are washed with sat. sodium hydrogencarbonate solution, dried over sodium sulfate, filtered and evaporated in vacuo. The residue gives 1-[3-fluoro-4-(3,4,5-trifluorophenyl)phenyl]-4-(5-propyl-1,3-dioxan-2-yl)cyclohexanol 5 as yellowish crystals.

Step 1.3: 2-[4-[3-Fluoro-4-(3,4,5-trifluorophenyl)phenyl]cyclohex-3-en-1-yl]-5-propyl-1,3-dioxane

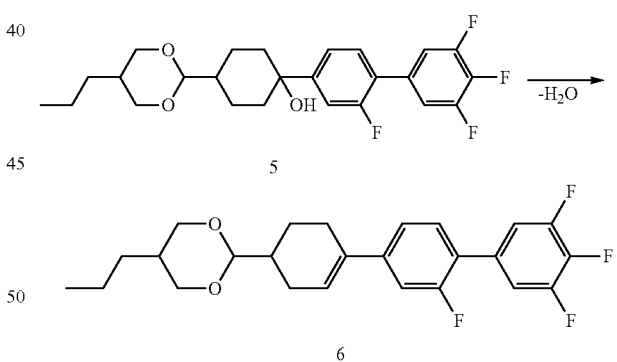

Toluene-4-sulfonic acid monohydrate (0.5 g, 3 mmol) is added to a solution of 1-[3-fluoro-4-(3,4,5-trifluorophenyl)phenyl]-4-(5-propyl-1,3-dioxan-2-yl)-cyclohexanol 5 (15.8 g, 15 mmol) in toluene (80 ml), and the mixture is heated under reflux on a water separator for 3 h. The reaction mixture is cooled to RT, diluted with heptane and chromatographed over silica gel (heptane/MTB ether 95:5). After crystallisation from 2-propanol and heptane, 2-[4-[3-fluoro-4-(3,4,5-trifluorophenyl)phenyl]cyclohex-3-en-1-yl]-5-propyl-1,3-dioxane 6 is isolated as a colourless solid. Compound 6 exhibits the following phase behaviour:

C 74 SmA 168 N 191 I.

Δε=30

Δn=0.18

Example 2

2[4-[3-Fluoro-4-(3,4,5-trifluorophenyl)phenyl]cyclohex-3-en-1-yl]-5-butyl-1,3-dioxane

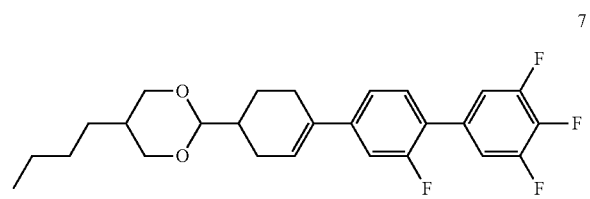 [SMILES: CCCCC1COC(C2CC=C(c3ccc(-c4cc(F)c(F)c(F)c4)c(F)c3)CC2)OC1]

7

2-[4-[3-Fluoro-4-(3,4,5-trifluorophenyl)phenyl]cyclohex-3-en-1-yl]-5-butyl-1,3-dioxane 7 is synthesised analogously to 2-[4-[3-fluoro-4-(3,4,5-trifluoro-phenyl)phenyl]cyclohex-3-en-1-yl]-5-propyl-1,3-dioxane 6. Compound 7 exhibits the following phase behaviour:
C 64 SmA 174 N 190 I.
$\Delta\varepsilon = 28$
$\Delta n = 0.18$

Example 3

2-[4-[4-[3,5-Difluoro-4-(trifluoromethyl)phenyl]-3-fluorophenyl]-cyclohex-3-en-1-yl]-5-propyl-1,3-dioxane

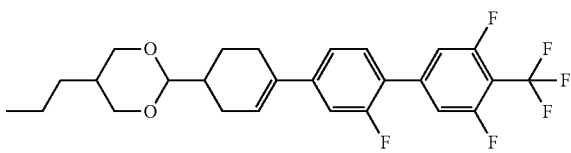

Step 3.1: [3,5-Difluoro-4-(trifluoromethyl)phenyl]boronic acid

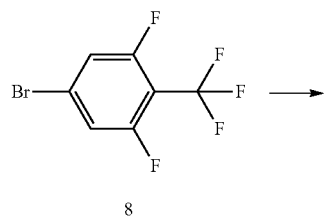

A solution of 5-bromo-1,3-difluoro-2-(trifluoromethyl)benzene 8 (CAS 156243-64-0, 200 g, 760 mmol) in THF (800 ml) is cooled to −5° C., and isopropylmagnesium chloride (420 ml, 840 mmol, 2.0 mol/l in THF) is added. After 1 h, a solution of trimethyl borate (106 ml, 950 mmol) in THF (100 ml) is added at −5° C., and the reaction mixture is stirred overnight at RT. The reaction mixture is added to ice-cold hydrochloric acid (410 ml, 2 M) and extracted with MTB ether. The phases are separated, the organic phase is washed with dist. water, dried over sodium sulfate, filtered and evaporated in vacuo. The crude product is purified by crystallisation from heptane, giving [3,5-difluoro-4-(trifluoromethyl)phenyl]boronic acid 9 as a beige solid.

Step 3.2: 5-(4-Bromo-2-fluorophenyl)-1,3-difluoro-2-(trifluoromethyl)-benzene

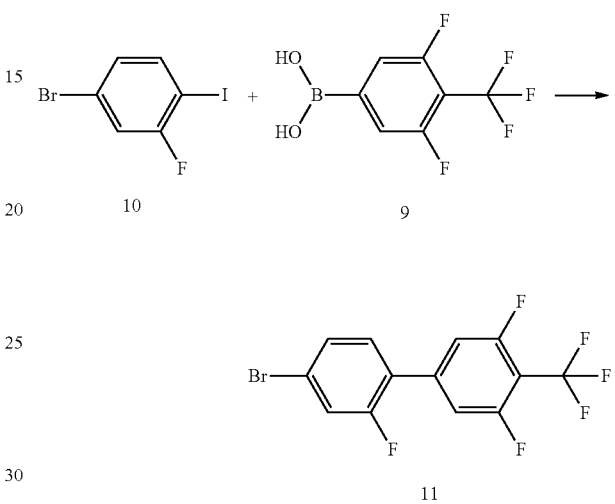

A solution of sodium metaborate tetrahydrate (8.9 g, 64 mmol) in dist. water (23 ml) is initially introduced, THF (10 ml), bis(triphenylphosphine)-palladium(II) chloride (15.2% Pd) (0.6 g, 0.9 mmol) and hydrazinium hydroxide (0.04 ml, 0.9 mmol) are added, and the mixture is stirred for 5 min. 4-Bromo-2-fluoro-1-iodobenzene 10 (CAS 105931-73-5, 12.7 g, 42 mmol), [3,5-difluoro-4-(trifluoromethyl)phenyl]boronic acid 9 (10.0 g, 42 mmol) and THF (40 ml) are then added, and the reaction mixture is refluxed overnight. Dist. water is added to the reaction mixture, which is then diluted with MTB ether. The aqueous phase is separated off and extracted with MTB ether. The combined organic phases are washed with sat. sodium chloride solution, dried over sodium sulfate, filtered and evaporated in vacuo. The crude product is chromatographed over silica gel (heptane), giving 5-(4-bromo-2-fluorophenyl)-1,3-difluoro-2-(trifluoromethyl)benzene 11 as a clear, colourless oil.

Step 3.3: 1-[4-[3,5-Difluoro-4-(trifluoromethyl)phenyl]-3-fluorophenyl]-4-(5-propyl-1,3-dioxan-2-yl)cyclohexanol

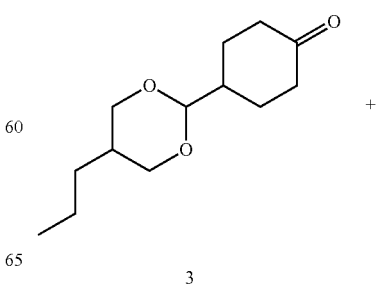

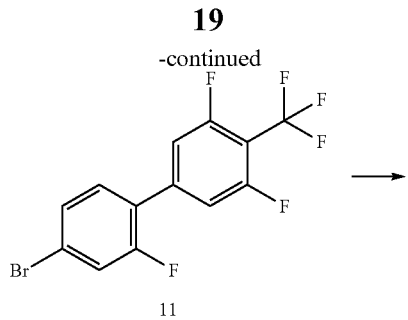

11

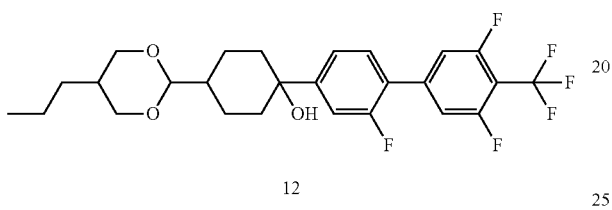

12

Isopropylmagnesium chloride (15.7 ml, 31.4 mmol, 2 mol/l in THF) is initially introduced, and a solution of 5-(4-bromo-2-fluorophenyl)-1,3-difluoro-2-(trifluoromethyl)benzene 11 (5.8 g, 15.7 mmol) in THF (50 ml) is added dropwise at 30° C. After 60 min, a solution of 4-(5-propyl-1,3-dioxan-2-yl)-cyclohexanone 3 (5.0 g, 15.7 mmol) in THF (15 ml) is added dropwise at a maximum of 20° C. After a further 60 min, dist. water is added to the reaction mixture, which is then adjusted to pH=5 using hydrochloric acid (1 M). The aqueous phase is separated off and extracted with MTB ether. The combined organic phases are washed with sat. sodium hydrogencarbonate solution, dried over sodium sulfate, filtered and evaporated in vacuo. The residue gives 1-[4-[3,5-difluoro-4-(trifluoromethyl)phenyl]-3-fluorophenyl]-4-(5-propyl-1,3-dioxan-2-yl)cyclohexanol 12 as a brownish crystal mass.

Step 3.4: 2-[4-[4-[3,5-Difluoro-4-(trifluoromethyl)phenyl]-3-fluorophenyl]-cyclohex-3-en-1-yl]-5-propyl-1,3-dioxane Toluene-4-sulfonic acid monohydrate (0.3 g, 1.6 mmol) is added to a solution of 1-[4-[3,5-difluoro-4-(trifluoromethyl)phenyl]-3-fluorophenyl]-4-(5-propyl-1,3-dioxan-2-yl)cyclohexanol 12 (10.1 g, 8.2 mmol) in toluene (45 ml), and the mixture is refluxed on a water separator for 2 h. The reaction mixture is cooled to RT, evaporated in vacuo and chromatographed over silica gel (heptane/MTB ether 95:5). After crystallisation from 2-propanol and n-heptane, 2-[4-[4-[3,5-difluoro-4-(trifluoromethyl)phenyl]-3-fluorophenyl]cyclohex-3-en-1-yl]-5-propyl-1,3-dioxane 13 is isolated as a colourless solid. Compound 13 exhibits the following phase behaviour:

C 124 SmA 173 N 186 I.

$\Delta\varepsilon = 38$ $\Delta n = 0.19$

Example 4

2-[4-[4-[3,5-Difluoro-4-(trifluoromethoxy)phenyl]-3-fluorophenyl]cyclohex-3-en-1-yl]-5-propyl-1,3-dioxane

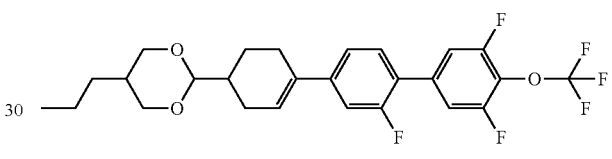

Step 4.1: 2-[3,5-Difluoro-4-(trifluoromethoxy)phenyl]-4,4,5,5-tetramethyl-1,3-dioxa-2-borolane

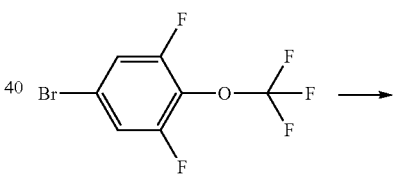

14

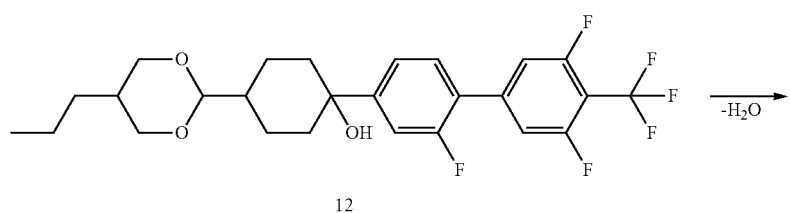

12

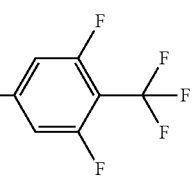

13

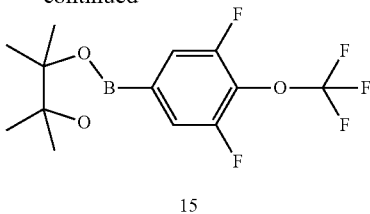

15

Potassium acetate (53.2 g, 540 mmol), 1,1'-bis(biphenylphosphine)-ferrocenepalladium dichloride (4.0 g, 5.4 mmol) and bis(pinacolato)diboron (70.2 g, 271 mmol) are added to a solution of 5-bromo-1,3-difluoro-2-(trifluoromethoxy)benzene 14 (CAS 115467-07-7, 50.0 g, 180 mmol) in 1,4-dioxane (430 ml), and the mixture is refluxed overnight. The reaction mixture is cooled to RT, dist. water is added, and the mixture is diluted with MTB ether. The phases are separated, the aqueous phase is extracted with MTB ether, the combined organic phases are washed with sat. sodium chloride solution, dried over sodium sulfate, filtered and evaporated in vacuo. The crude product is chromatographed over silica gel (toluene) and crystallised from ethanol, giving 2-[3,5-difluoro-4-(trifluoro-methoxy)phenyl]-4,4,5,5-tetramethyl-1,3-dioxa-2-borolane 15 as a colourless solid.

Step 4.2: 5-(4-Bromo-2-fluorophenyl)-1,3-difluoro-2-(trifluoromethoxy)-benzene

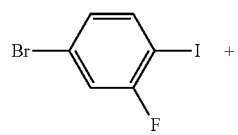

10

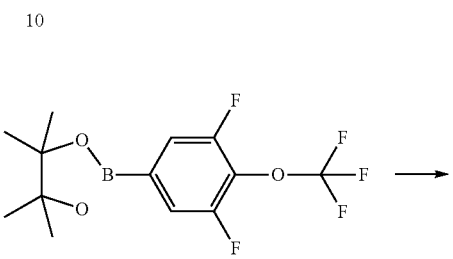

15

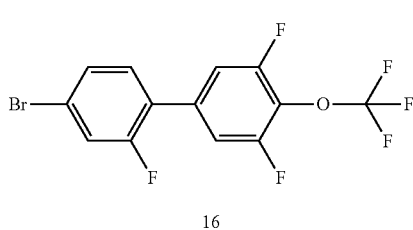

16

A solution of sodium metaborate tetrahydrate (10.2 g, 74 mmol) in dist. water (33.2 ml) is initially introduced, THF (10 ml), bis(triphenylphosphine)-palladium(II) chloride (15.2% Pd) (1.7 g, 2.5 mmol) and hydrazinium hydroxide (0.12 ml, 2.5 mmol) are added, and the mixture is stirred for 5 min. 4-Bromo-2-fluoro-1-iodobenzene 10 (18.5 g, 61 mmol), 2-[3,5-difluoro-4-(trifluoromethoxy)phenyl]-4,4,5,5-tetramethyl-1,3-dioxa-2-borolane 15 (20.0 g, 61 mmol) and THF (65 ml) are then added, and the reaction mixture is refluxed overnight. Dist. water is added to the reaction mixture, which is then diluted with MTB ether. The aqueous phase is separated off and extracted with MTB ether. The combined organic phases are washed with sat. sodium chloride solution, dried over sodium sulfate, filtered and evaporated in vacuo. The crude product is chromatographed over silica gel (heptane) and recrystallised from heptane, giving 5-(4-bromo-2-fluorophenyl)-1,3-difluoro-2-(trifluoromethoxy)benzene 16 as a colourless solid.

Step 4.3: 1-[4-[3,5-Difluoro-4-(trifluoromethoxy)phenyl]-3-fluorophenyl]-4-(5-propyl-1,3-dioxan-2-yl)cyclohexanol

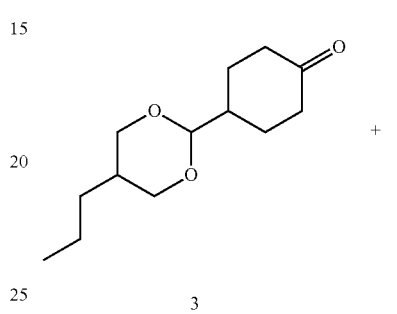

3

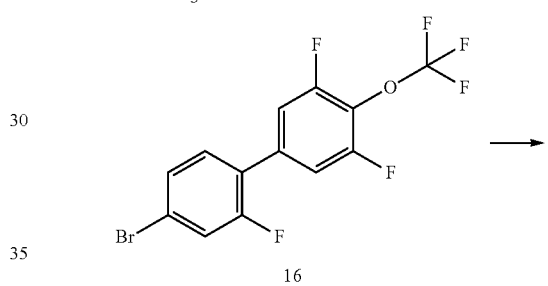

16

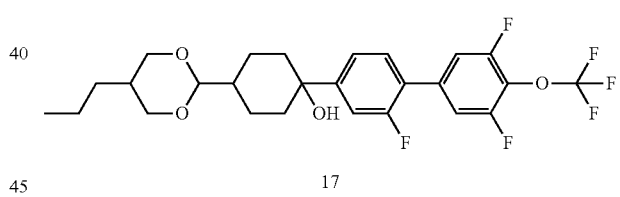

17

Isopropylmagnesium chloride/lithium chloride (23.7 ml, 30.8 mmol, 1.3 mol/l in THF) is initially introduced, and a solution of 5-(4-bromo-2-fluoro-phenyl)-1,3-difluoro-2-(trifluoromethoxy)benzene 16 (5.5 g, 14.6 mmol) in THF (25 ml) is added dropwise at 30° C. After 60 min, a solution of 4-(5-propyl-1,3-dioxan-2-yl)cyclohexanone 3 (5.0 g, 15.4 mmol) in THF (37 ml) is added dropwise at the maximum of 20° C., and the mixture is stirred overnight. Dist. water is then added to the reaction mixture, which is then adjusted to pH=5 using hydrochloric acid (1 M). The aqueous phase is separated off and extracted with MTB ether. The combined organic phases are washed with sat. sodium hydrogencarbonate solution, dried over sodium sulfate, filtered and evaporated in vacuo. The residue gives 1-[4-[3,5-difluoro-4-(trifluoromethoxy)phenyl]-3-fluorophenyl]-4-(5-propyl-1,3-dioxan-2-yl)cyclohexanol 17 as a yellow crystal mass.

Step 4.4: 2-[4-[4-[3,5-Difluoro-4-(trifluoromethoxy)phenyl]-3-fluorophenyl]-cyclohex-3-en-1-yl]-5-propyl-1,3-dioxane

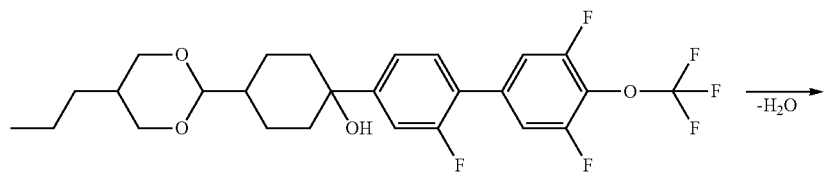

17

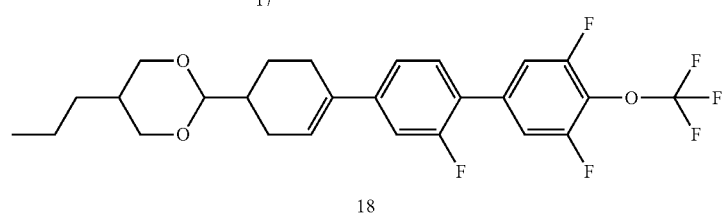

18

Toluene-4-sulfonic acid monohydrate (0.3 g, 2.0 mmol) is added to a solution of 1-[4-[4-[3,5-difluoro-4-(trifluoromethoxy)phenyl]-3-fluorophenyl]-4-(5-propyl-1,3-dioxan-2-yl]cyclohexanol 17 (10.8 g, 9.9 mmol) in toluene (53 ml), and the mixture is refluxed on a water separator for 2 h. The reaction mixture is cooled to RT, evaporated in vacuo and chromatographed over silica gel (heptane/MTB ether 95:5). After crystallisation from 2-propenyl and heptane, 2-[4-[4-[3,5-difluoro-4-(trifluoromethoxy)phenyl]-3-fluorophenyl]cyclohex-3-en-1-yl]-5-propyl-1,3-dioxane 18 is isolated as a colourless solid. Compound 18 exhibits the following phase behaviour:
C 95 Sm 213 I.
Δε=30
Δn=0.18

Example 5

2-[4-[3-Fluoro-4-(3,4,5-trifluorophenyl)phenyl]cyclohex-3-en-1-yl]-5-propyltetrahydropyran

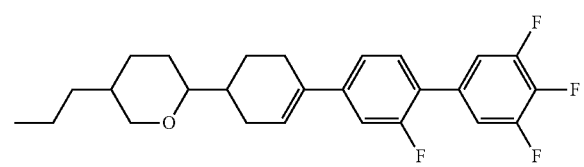

Step 5.1: 4-(5-Propyltetrahydropyran-2-yl)cyclohexanone

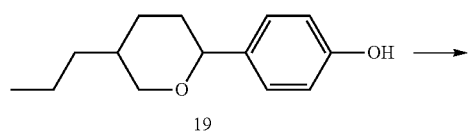

4-(5-Propyltetrahydropyran-2-yl)phenol 19 (CAS 879544-24-8, 50.0 g, 227 mmol) is dissolved in xylene (330 ml), Pd/C (5%, 4.4 g) and sodium carbonate (0.2 g, 2.3 mmol) are added, and the mixture is hydrogenated under pressure using hydrogen (10.2 l). After 8 h, the solution is filtered and evaporated in vacuo. The crude product is taken up in n-heptane (200 ml), a mixture of sulfur trioxide/pyridine complex (37.0 g, 233 mmol) and Celite (50 g) is added, and the mixture is stirred overnight at RT. Further Celite (20 g) and silica gel (20 g) are then added, and the mixture is stirred. After 90 min, the reaction mixture is filtered with suction. The filtrate is washed with dist. water and sat. sodium hydrogencarbonate solution, dried over sodium sulfate, filtered and evaporated in vacuo. The residue gives 4-(5-propyltetrahydropyran-2-yl)cyclohexanone 20 as a clear, yellowish oil.

Step 5.2: 1-[3-Fluoro-4-(3,4,5-trifluorophenyl)phenyl]-4-(5-propyltetrahydro-pyran-2-yl)cyclohexanol

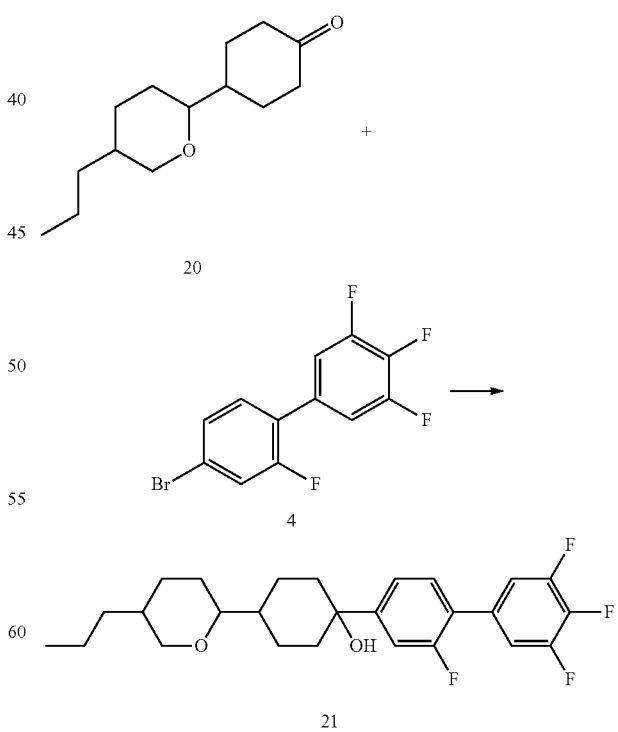

A solution of isopropylmagnesium chloride (22.9 ml, 46 mmol, 2.0 mol/l in THF) is initially introduced, and a solution of 5-(4-bromo-2-fluorophenyl)-1,2,3-trifluorobenzene 4 (7.0 g, 23 mmol) in THF (50 ml) is added dropwise at 30° C. After 60 min, a solution of 4-(5-propyltetrahydropyran-2-yl)cyclohexanone 20 (5.1 g, 23 mmol) in THF (50 ml) is added dropwise at a maximum of 30° C. After a further 60 min, dist. water is added to the reaction mixture, which is then adjusted to pH=5 using hydrochloric acid (1 M).

The aqueous phase is separated off and extracted with MTB ether. The combined organic phases are washed with sat. sodium hydrogencarbonate solution, dried over sodium sulfate, filtered and evaporated in vacuo. The residue gives 1-[3-fluoro-4-(3,4,5-trifluorophenyl)phenyl]-4-(5-propyl-tetra-hydropyran-2-yl)cyclohexanol 21 as yellowish crystals.

Step 5.3: 2-[4-[3-Fluoro-4-(3,4,5-trifluorophenyl)phenyl] cyclohex-3-en-1-yl]-5-propyl-tetrahydropyran Toluene-4-sulfonic acid monohydrate (0.5 g, 3 mmol) is added to a solution of 1-[3-fluoro-4-(3,4,5-trifluorophenyl)phenyl]-4-(5-propyltetrahydropyran-2-yl)cyclohexanol 21 (12.2 g, 15 mmol) in toluene (80 ml), and the mixture is refluxed on a water separator for 90 min. The reaction mixture is cooled to RT, diluted with n-heptane and chromatographed over silica gel (heptane/MTB ether 95:5). After recrystallisation from 2-propanol and n-heptane, 2-[4-[3-fluoro-4-(3,4,5-trifluorophenyl)phenyl]cyclohex-3-en-1-yl]-5-propyltetrahydropyran 22 is isolated in the form of colourless crystals. Compound 22 exhibits the following phase behaviour:
C 95 N 191 I.
Δε=23
Δn=0.17

Example 6

2-[4-[4-[3,5-Difluoro-4-(trifluoromethyl)phenyl]-3-fluorophenyl]-cyclohex-3-en-1-yl]-5-propyl-tetrahydropyran

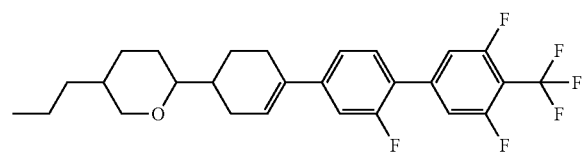 [SMILES: CCCC1COC(C2CC=C(c3ccc(-c4cc(F)c(C(F)(F)F)c(F)c4)c(F)c3)CC2)OC1]

Step 6.1: 1-[4-[3,5-Difluoro-4-(trifluoromethyl)phenyl]-3-fluorophenyl]-4-(5-propyltetrahydropyran-2-yl)cyclohexanol

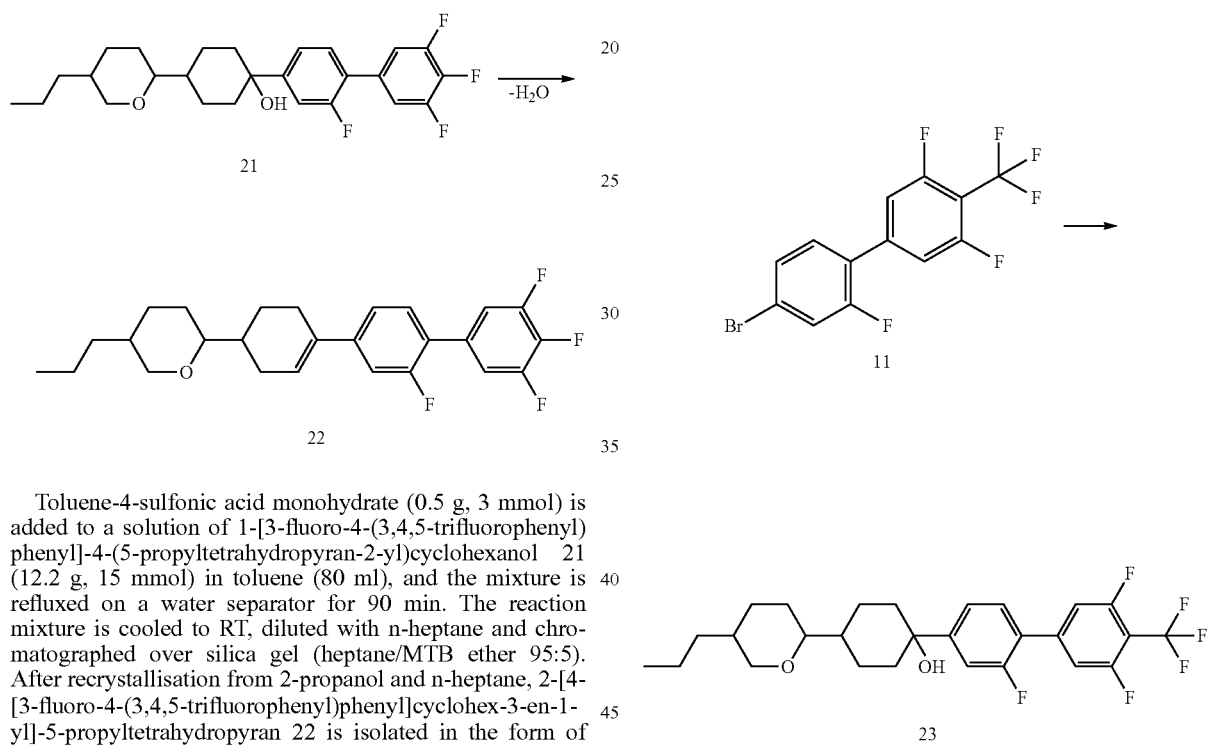

Isopropylmagnesium chloride (10.8 ml, 22 mmol, 2 mol/l in THF) is initially introduced and a solution of 5-(4-bromo-2-fluorophenyl)-1,3-difluoro-2-(trifluoromethyl)benzene 11 (4.0 g, 11 mmol) in THF (20 ml) is added dropwise at 30° C. After 60 min, a solution of 4-(5-propyltetrahydropyran-2-yl)-cyclohexanone 20 (2.5 g, 11 mmol) in THF (15 ml) is added dropwise at a maximum of 20° C. After a further 60 min, dist. water is added to the reaction mixture, which is then adjusted to pH=5 using hydrochloric acid (1 M). The aqueous phase is separated off and extracted with MTB ether.

The combined organic phases are washed with sat. sodium hydrogencarbonate solution, dried over sodium sulfate, filtered and evaporated in vacuo. The residue gives 1-[4-[3,5-difluoro-4-(trifluoromethyl)phenyl]-3-fluorophenyl]-4-(5-propyltetrahydropyran-2-yl)cyclohexanol 23 as a yellowish crystal mass.

Step 6.2: 2-[4-[4-[3,5-Difluoro-4-(trifluoromethyl)phenyl]-3-fluorophenyl]-cyclohex-3-en-1-yl]-5-propyltetrahydropyran

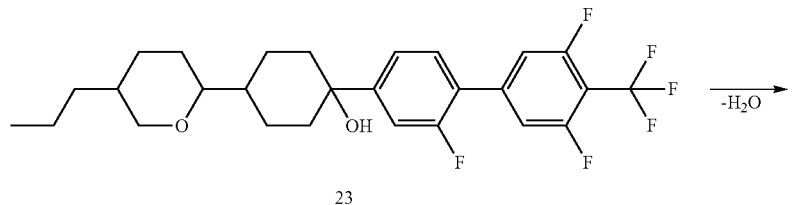

23

-H₂O →

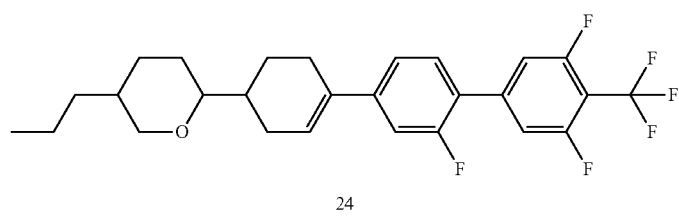

24

Toluene-4-sulfonic acid monohydrate (0.3 g, 1.5 mmol) is added to a solution of 1-[4-[3,5-difluoro-4-(trifluoromethyl)phenyl]-3-fluorophenyl]-4-(5-propyltetrahydropyran-2-yl)cyclohexanol 23 (7.1 g, 7 mmol) in toluene (40 ml), and the mixture is refluxed on a water separator for 2 h. The reaction mixture is cooled to RT, evaporated in vacuo and chromatographed over silica gel (heptane/MTB ether 95:5). After crystallisation from 2-propanol and n-heptane, 2-[4-[4-[3,5-difluoro-4-(trifluoromethyl)phenyl]-3-fluorophenyl]cyclohex-3-en-1-yl]-5-propyltetrahydropyran 24 is isolated in the form of colourless crystals. Compound 24 exhibits the following phase behaviour:

C 98 N 182 I.

Δε=31

Δn=0.19

Example 7

2-[4-[4-[3,5-Difluoro-4-(trifluoromethoxy)phenyl]-3-fluorophenyl]cyclohex-3-en-1-yl]-5-propyltetrahydropyran Step 7.1: 1-[4-[3,5-Difluoro-4-(trifluoromethoxy)phenyl]-3-fluorophenyl]-4-(5-propyltetrahydropyran-2-yl)cyclohexanol

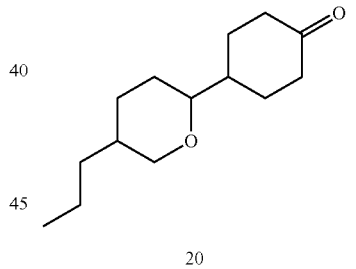

20

+

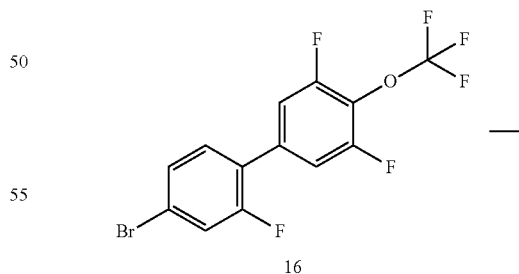

16

→

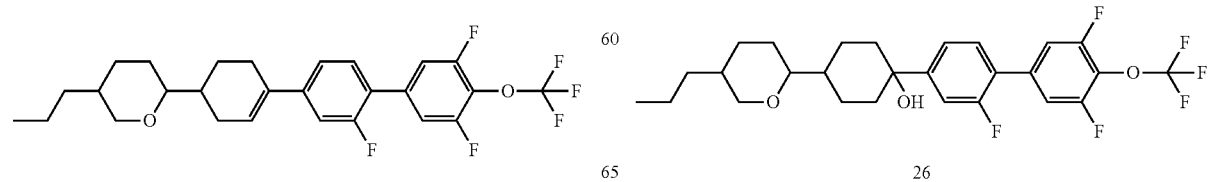

Isopropylmagnesium chloride (13.1 ml, 26 mmol, 2.0 mol/l in THF) is initially introduced, and a solution of 5-(4-bromo-2-fluorophenyl)-1,3-difluoro-2-(trifluoromethoxy)benzene 16 (5.0 g, 13 mmol) in THF (25 ml) is added dropwise at 30° C. After 60 min, a solution of 4-(5-propyltetrahydropyran-2-yl)cyclohexanone 20 (3.0 g, 13 mmol) in THF (37 ml) is added dropwise at a maximum of 20° C., and the mixture is stirred overnight. Dist. water is then added to the reaction mixture, which is then adjusted to pH=5 using hydrochloric acid (1 M). The aqueous phase is separated off and extracted with MTB ether. The combined organic phases are washed with sat. sodium hydrogencarbonate solution, dried over sodium sulfate, filtered and evaporated in vacuo. The residue gives 1-[4-[3,5-difluoro-4-(trifluoromethoxy)phenyl]-3-fluorophenyl]-4-(5-propyltetrahydropyran-2-yl)cyclohexanol 26 as a yellowish oil.
Step 7.2: 2-[4-[4-[3-Difluoro-4-(trifluoromethoxy)phenyl]-3-fluorophenyl]-cyclohex-3-en-1-yl]-5-propyltetrahydropyran

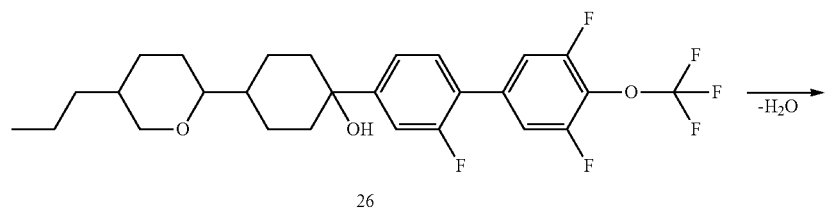

26

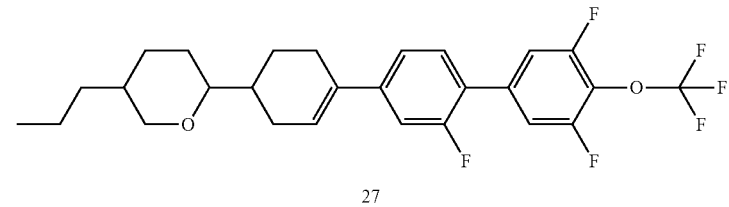

27

Toluene-4-sulfonic acid monohydrate (0.3 g, 2 mmol) is added to a solution of 1-[4-[3,5-difluoro-4-(trifluoromethoxy)phenyl]-3-fluorophenyl]-4-(5-propyltetrahydropyran-2-yl)cyclohexanol 26 (8.7 g, 8 mmol) in toluene (40 ml), and the mixture is refluxed on a water separator for 2 h. The reaction mixture is cooled to RT, evaporated in vacuo and chromatographed over silica gel (heptane/MTB ether 95:5). After crystallisation from 2-propanol and n-heptane, 2-[4-[4-[3,5-difluoro-4-(trifluoromethoxy)phenyl]-3-fluorophenyl]cyclohex-3-en-1-yl]-5-propyl-tetrahydropyran 27 is isolated as a colourless solid. Compound 27 exhibits the following phase behaviour:

C 78 Sm 117 N 206 I

Δε=24

Δn=0.18

The following are prepared analogously:

Example 8

2-[4-[3-Fluoro-4-(2-methyl-3,4,5-trifluorophenyl)phenyl]cyclo-hex-3-en-1-yl]-5-propyl-1,3-dioxane

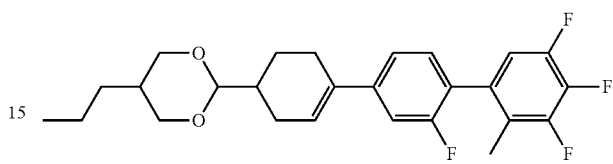

Example 9

2-[4-[3-Fluoro-4-(2-methyl-3,4,5-trifluorophenyl)phenyl]cyclo-hex-3-en-1-yl]-5-propyltetrahydropyran

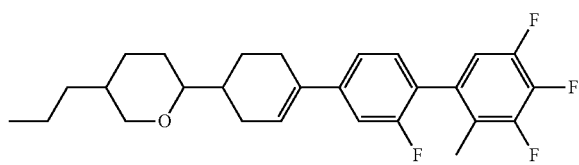 [SMILES: CCCC1CCC(C2CC=C(c3ccc(-c4cc(F)c(F)c(F)c4C)c(F)c3)CC2)OC1]

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever. The preceding examples can be repeated with similar success by substituting the generically or specifically described reactants and/or operating conditions of this invention for those used in the preceding examples.

The entire disclosures of all applications, patents and publications, cited herein and of corresponding German application No. 102019001887.7, filed Mar. 18, 2019, are incorporated by reference herein.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of the formula I,

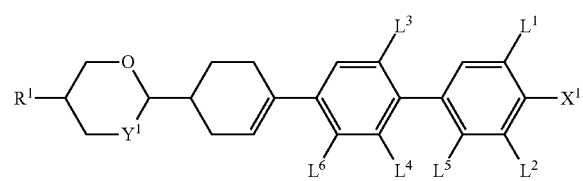

in which $X^1$ denotes F, $CF_3$, $OCF_3$, Cl, $OCHF_2$, $CHF_2$, SCN or CN, $Y^1$ denotes O or $CH_2$, $R^1$ denotes an alkyl radical having 1 to 15 C atoms, where one or more $CH_2$ groups in these radicals are optionally replaced, independently of one another, by —C≡C—, —CH=CH—

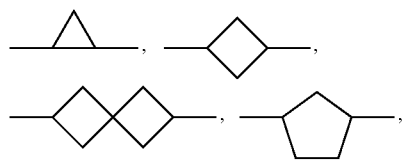

—S—, —CO—O— or —O—CO— in such a way that O and S atoms are not linked directly to one another, and in which one or more H atoms are optionally replaced by halogen, $L^1$ and $L^2$, independently of one another, denote H or F, $L^3$ denotes H or F, $L^4$ denotes H or F, and $L^5$ and $L^6$, independently of one another, denote H or $CH_3$.

2. A compound according to claim 1, wherein $L^4$ denotes H.

3. A compound according to claim 1, wherein $R^1$ denotes alkyl having 1 to 8 carbon atoms or alkenyl having 2 to 8 carbon atoms.

4. A compound according to claim 1, wherein $X^1$ denotes F, $OCF_3$ or $CF_3$.

5. A compound according to claim 1, wherein $L^1$ and $L^2$ each denote F.

6. A compound according to claim 1, wherein $Y^1$ denotes O.

7. A compound according to claim 1, wherein $Y^1$ denotes $CH_2$.

8. A compound according to claim 1 selected from compounds of the following formulae:

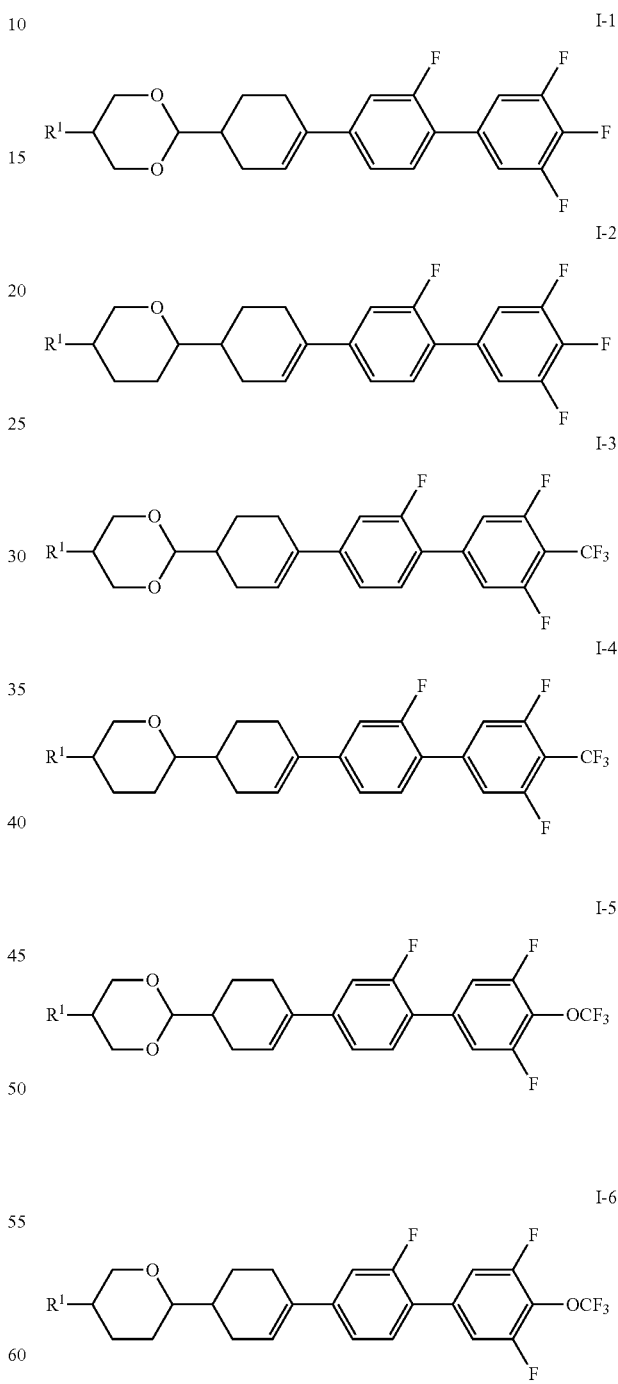

in which $R^1$ has the meanings indicated in claim 1.

9. A compound according to claim 1, wherein $R^1$ denotes a straight-chain alkyl radical having 1 to 7 C atoms or an unbranched alkenyl radical having 2 to 8 C atoms.

10. A process for the preparation of a compound of formula I according to claim 1, which comprises:
reacting an arylhalogen compound of the formula II

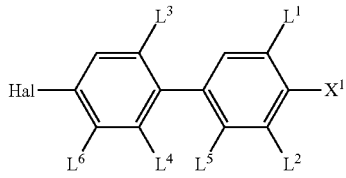
II in which $X^1$, $L^1$, $L^2$, $L^3$ and $L^4$ are as defined in claim 1, and
Hal denotes Br, I or Cl,
with a compound of the formula III

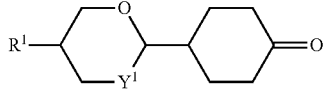
III in which
in which $R^1$ and $Y^1$ are as defined in claim 1,
to give a compound of the formula IV,

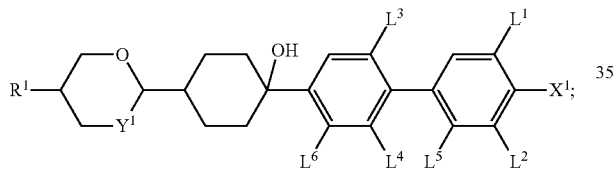
IV and converting the compound of formula IV into a compound of the formula I

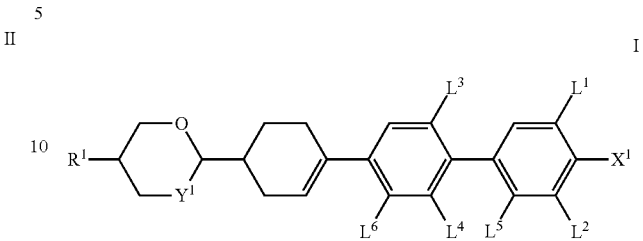
I in which the groups $R^1$, $Y^1$, $L^1$, $L^2$, $L^3$, $L^4$ and $X^1$ are as defined in claim 1.

11. A liquid-crystalline medium comprising at least two mesogenic compounds, which comprises at least one compound of the formula I according to claim 1.

12. Electro-optical liquid-crystal display comprising a liquid-crystalline medium according to claim 11.

13. A compound according to claim 8, wherein $R^1$ denotes alkyl having 1 to 8 carbon atoms or alkenyl having 2 to 8 carbon atoms.

14. A compound according to claim 1, wherein:
$L^4$ and $L^5$ each denote H;
$R^1$ denotes alkyl having 1 to 8 carbon atoms or alkenyl having 2 to 8 carbon atoms;
$X^1$ denotes F, $OCF_3$ or $CF_3$; and
$L^1$ and $L^2$ each denote F.

15. A compound according to claim 1, wherein $L^5$ denotes H.

* * * * *